(12) United States Patent
Notoya

(10) Patent No.: US 7,592,591 B2
(45) Date of Patent: Sep. 22, 2009

(54) X-RAY ANALYZER USING ELECTRON BEAM

(75) Inventor: Satoshi Notoya, Tokyo (JP)

(73) Assignee: Jeol Ltd., Tokyo (JP)

( * ) Notice: Subject to any disclaimer, the term of this patent is extended or adjusted under 35 U.S.C. 154(b) by 289 days.

(21) Appl. No.: 11/784,686

(22) Filed: Apr. 9, 2007

(65) Prior Publication Data

US 2008/0067379 A1 Mar. 20, 2008

(30) Foreign Application Priority Data

Apr. 14, 2006 (JP) .............................. 2006-111493

(51) Int. Cl.
*H01J 37/26* (2006.01)
(52) U.S. Cl. ................... 250/310; 250/306; 250/307; 378/46; 378/82; 378/83; 378/86; 378/87; 378/88; 378/90
(58) Field of Classification Search ................ 250/306, 250/307, 310, 311, 305, 308, 309, 492.1, 250/492.2, 492.3; 378/46, 49, 45, 48, 82, 378/83, 85, 86, 87, 88, 89, 90
See application file for complete search history.

(56) References Cited

U.S. PATENT DOCUMENTS 4,988,872 A * 1/1991 Nagatsuka et al. ............. 850/9
5,299,138 A * 3/1994 Fiori et al. .................... 702/22
5,912,940 A * 6/1999 O'Hara ......................... 378/82
6,292,532 B1 * 9/2001 Kawahara et al. ............. 378/49
6,546,069 B1 * 4/2003 Martin ......................... 378/49

FOREIGN PATENT DOCUMENTS

| JP | 3547310 | 10/1999 |
| JP | 2002-357571 | * 12/2002 |
| JP | 2006-58015 | * 3/2006 |

* cited by examiner

Primary Examiner—Jack I Berman
Assistant Examiner—Nicole Ippolito Rausch
(74) Attorney, Agent, or Firm—The Webb Law Firm

(57) ABSTRACT

An electron probe X-ray analyzer capable of automatically setting appropriate analytical conditions if there are unknown compounds by performing analysis under the analytical conditions adapted for analysis points having different compositions in a case where the numerous analysis points having the plural compositions are analyzed by WDS (wavelength-dispersive X-ray spectrometer). At each analysis point, the analyzer performs quantitative analysis using EDS (energy-dispersive X-ray spectrometer) permitting easy and quick analysis. Based on the results, chemical compounds are identified. If the results indicate that there is any new compound, analytical conditions adapted for the new compound are selected. If the new compound is already registered in a database, the analytical conditions are read from the database. Then, quantitative analysis is performed using WDS.

7 Claims, 4 Drawing Sheets

X-RAY ANALYZER USING ELECTRON BEAM

BACKGROUND OF THE INVENTION

1. Field of the Invention

The present invention relates to an electron probe X-ray analyzer for performing elemental analysis using characteristic X-rays, such as an electron probe microanalyzer (EPMA) or analytical scanning electron microscope (analytical SEM) equipped with a wavelength-dispersive X-ray spectrometer (WDS) and an energy-dispersive X-ray spectrometer (EDS). More particularly, the invention relates to an analytical technique for identifying the composition of a sample.

2. Description of Related Art

EPMAs and analytical SEMs are instruments for analyzing samples by directing a sharply focused, accelerated electron beam at the samples and using the produced characteristic X-rays. These instruments are all known as electron probe X-ray analyzers. X-ray spectrometers attached to electron probe X-ray analyzers for spectrally analyzing and detecting X-rays produced from samples are classified into two major categories: WDS (wavelength-dispersive spectrometer) and EDS (energy-dispersive spectrometer). The WDS is a spectrometer for detecting with an X-ray detector only X-rays satisfying the Bragg reflection conditions by the use of an analyzing crystal. An X-ray spectrum is obtained by measuring the intensity of X-rays incident on the analyzing crystal, the intensity varying according to the incident angle of the X-rays. In contrast, the EDS is a spectrometer for obtaining an X-ray spectrum by converting X-rays incident on a semiconductor detector, such as a PIN detector into an electrical signal, guiding pulses having heights proportional to the energies of the incident X-rays to a multichannel analyzer, and accumulating the number of pulses for each of channels corresponding to X-ray energies.

Because of the difference in principle and structure between both kinds of spectrometers, analyses performed using WDS and EDS, respectively, have their features. For example, WDS can perform analysis with high wavelength resolution, high P/B (peak/background) ratio, and high count rate capability. Therefore, WDS is adapted for low-concentration analysis and analysis of chemical-bonding states. However, in order to analyze plural elements at the same time, it is necessary to equip corresponding plural spectrometers. Furthermore, plural kinds of analyzing crystals need to be mounted on each one spectrometer. Therefore, WDS has limited capabilities of performing easy and quick analyses.

Meanwhile, EDS can analyze multiple elements at the same time with a single detector. Furthermore, EDS has the advantage over WDS that the detector is not required to be driven mechanically for X-ray spectroscopy. However, EDS is inferior in energy resolution (corresponding to wavelength resolution of WDS) and P/B ratio of X-ray spectra to WDS. Additionally, in principle, EDS has the restriction that the efficiency at which only a certain X-ray is detected cannot be enhanced because of simultaneous analysis of multiple elements with a single detector. Therefore, EDS has restricted capabilities of performing low-concentration analysis and analysis of chemical-bonding states.

Therefore, taking account of the features of WDS and EDS, WDS is mainly fitted to EPMA while EDS is chiefly fitted to analytical SEM. In addition, many instruments are equipped with both WDS and EDS to make effective use of both WDS and EDS and to improve the analyzing capabilities and operability of the whole instrument. One known system has both a WDS system and an EDS system in a simple manner, and each system is separately operated to perform analysis. In another known system, WDS and EDS are controlled in an interrelated manner by a single control system to perform analysis (see, for example, Japanese Patent Laid-Open No. H2-47542). This system may be termed a "WDS/EDS combined system".

A technique for identifying a compound present at a point of analysis from the results of quantitative analysis of a sample using EPMA or the like is disclosed in Japanese Patent Laid-Open No. 2000-266700. A technique associated with quantitative analysis of a particulate sample using EPMA or the like is disclosed in Japanese Patent Laid-Open No. 2001-27621. In this technique, a chemical type is judged from the features of the chemical composition at a point of analysis. The chemical type is made to correspond to the position and morphology of the point of analysis and is displayed.

Where quantitative analysis is performed using EDS alone, if the sample contains many elements in trace amounts, it is difficult to obtain accurate quantitative analysis results because of limitations in energy resolution and P/B ratio of EDS. Therefore, where quite highly accurate analysis results are required even from comparatively low concentrations of elements such as found in geological and mineralogical applications, if an instrument having both WDS and EDS is used, analysis will be eventually performed using only WDS.

When a relatively low concentration of elements is analyzed quantitatively by WDS, attention must be paid especially to the position of the wavelength at which the background intensity is measured (hereinafter may be referred to as the background intensity measurement wavelength). In particular, if the characteristic X-rays of other coexisting elements (known as interfering lines) are present near the background intensity measurement wavelength, it is impossible to find the intensity of the characteristic X-rays accurately by the effects of the interfering lines. This deteriorates the reliability of the results of the analysis. Where plural points of analysis are analyzed quantitatively using WDS alone, if the main components at plural points are similar, it is not difficult to determine the background intensity measurement wavelength without being affected by the interfering lines, for example, by the use of the technique disclosed in Japanese Patent No. 3,547,310. Where the interfering lines are X-ray diffractions of the second or higher orders (higher-order reflections), the higher-order diffraction lines (interfering lines) can be removed by a pulse height analyzer (PHA) equipped to the X-ray counter circuit (see, for example, Japanese Patent Laid-Open No. H2-25787).

Meanwhile, with respect to modern electron probe X-ray analyzers, such as EPMA, automation of analyzing functions using computer control is in progress. Therefore, many analysis points to be analyzed, for example, quantitatively, are stored in memory in advance. Measurement and arithmetic processing, such as calculations for quantitative corrections, can be performed automatically. However, such many analysis points often contain plural phases having different main constituents. In such cases, interfering lines appear differently. In the past, when such many analysis points are analyzed continuously, it has been possible to have only one set of analytical conditions (hereinafter may be referred to as the PHA operating conditions) under which the pulse height analyzer (PHA) is operated to remove the background intensity measurement wavelengths of the elements and higher-order diffraction lines creating interfering lines. Therefore, the human operator has searched for analytical conditions not affected by interfering lines at any analysis point, e.g., by preliminarily measuring some probable analysis points of plural phases, to determine one set of PHA operating conditions. This work placed a heavy burden on the operator if the technique disclosed in Japanese Patent No. 3,547,310 or Japanese Patent Laid-Open No. H2-25787 is used. In addition, if there is an analysis point having unexpected composition during analysis, there is the possibility that correct analysis cannot be performed.

SUMMARY OF THE INVENTION

It is an object of the present invention to provide an electron probe X-ray analyzer which is free of the foregoing problems and which, where many analysis points having plural compositions are analyzed by WDS, performs analysis under analytical conditions adapted for the analysis points of the different compositions. The analyzer can automatically set appropriate analytical conditions if unknown components are present.

A first embodiment of the present invention is free of the foregoing problems and provides an electron probe X-ray analyzer for analyzing a sample by directing a sharply focused, accelerated electron beam at the sample and detecting produced characteristic X-rays. The X-ray analyzer has (i) WDS quantitative means for performing quantitative analysis using a wavelength-dispersive X-ray spectrometer (WDS) and (ii) EDS quantitative means for performing quantitative analysis using an energy-dispersive X-ray spectrometer (EDS). The electron probe X-ray analyzer comprises: (A) identification means for identifying compounds at analysis points (X-Y positions) from the results of quantitative analysis performed by the energy-dispersive X-ray spectrometer, (B) condition-setting means for setting analytical conditions under which quantitative analysis is performed by the wavelength-dispersive X-ray spectrometer at the analysis points based on the results of the identification of the compounds performed by the identification means, and (C) storage means for storing (i) data about the compounds at the analysis points identified by the identification means, (ii) the analytical conditions set by the condition-setting means, and (iii) the results of the measurement at the analysis points performed under the analytical conditions set by the condition-setting means such that these three sets of items are interrelated.

A second embodiment of the present invention is based on the first embodiment and further characterized in that the identification means compares the results of the quantitative analysis obtained by the WDS quantitative means against a compound database to identify the compounds at the analysis points. Compounds identified based on information about chemical compositions characterizing the compounds are registered in the compound database.

A third embodiment of the present invention is based on the first or second embodiment and further characterized in that the analytical conditions set by the condition-setting means based on the results of the identification of compounds identified by the identification means and stored in the storage means are used as analytical conditions under which quantitative analysis of a next analysis point is performed by the wavelength-dispersive X-ray spectrometer.

A fourth embodiment of the present invention is based on any one of the first through third embodiments and further characterized in that the analytical conditions set by the condition-setting means include at least one of (i) PHA operating conditions under which a pulse height analyzer (PHA) is set to remove background intensity measurement positions higher-order diffraction lines and (ii) peak intensity measurement wavelength positions determined by detection of peak wavelength positions.

A fifth embodiment of the present invention is based on any one of the first through fourth embodiments and further characterized in that the results of the measurement of the analysis points measured under the analytical conditions set by the condition-setting means include at least background intensities measured at the background intensity measurement wavelength positions.

A sixth embodiment of the present invention is based on any one of the first through fifth embodiments and further characterized in that the WDS quantitative means makes a decision as to whether measurement of the background intensities is performed or not, based on information about the identification of compounds at the analysis points identified by the identification means.

A seventh embodiment of the present invention is based on any one of the first through sixth embodiments and further characterized in that when the decision is made as to whether measurement of the background intensities is performed or not, the measurement of the background intensities is omitted when the compounds at the analysis points identified by the identification means have been already registered in the compound database.

In the first embodiment described above, where plural analysis points having different compositions are analyzed using the wavelength-dispersive spectrometer, analytical conditions adapted for the compositions, respectively, are automatically selected and reliable analysis can be performed. Furthermore, if a novel compound exists during the analysis, analytical conditions adapted for the novel compound can be automatically set and analysis can be performed. The efficiency at which analytical conditions are selected can be enhanced by storing those analytical conditions in memory.

In the second embodiment described above, compounds can be identified efficiently by making use of the energy-dispersive X-ray spectrometer permitting simple and quick analysis as well as the accumulated compound database.

In the third embodiment described above, analytical conditions adapted for quantitative analysis of compounds at analytical points using the wavelength-dispersive X-ray spectrometer can be selected by utilizing the energy-dispersive X-ray spectrometer permitting easy and quick analysis, the accumulated compound database, and a database newly accumulated during continuous analysis. Hence, reliable analysis can be performed.

In the fourth embodiment described above, the analytical conditions set by the condition-setting means include at least one of: (i) PHA operating conditions under which background intensity measurement wavelength positions and higher-order diffraction lines are removed and (ii) peak intensity measurement wavelength positions determined by detection of peak wavelength positions. Therefore, the analytical conditions under which quantitative analysis is performed by the wavelength-dispersive X-ray spectrometer offer new data during continuous analysis, and the new data can be added to the database. Analytical conditions under which the next analysis point is analyzed can be determined efficiently.

In the fifth embodiment described above, data newly collected on the background intensities during analysis of numerous points using the wavelength-dispersive X-ray spectrometer can be added to the database. If there are analysis points that are judged to lie in the same compound, measurement of the background intensities can be omitted.

In the sixth embodiment described above, the decision as to whether the measurement of the background intensities is performed or not using the wavelength-dispersive X-ray spectrometer (WDS) can be made efficiently by making use of the EDS permitting easy and quick analysis and an accumulated compound database.

In the seventh embodiment described above, in a case where a decision is made as to whether measurement of the background intensities is carried out or not, the measurement is omitted when compounds at the analysis points identified by the identification means are already registered in the compound database. Therefore, the measurement of the background intensities which would otherwise require the wavelength-dispersive X-ray spectrometer to be mechanically driven and which would take a longer time than to measure peak intensities can be omitted by utilizing the energy-dispersive X-ray spectrometer permitting easy and quick analysis and the accumulated compound database. Consequently, the throughput in measurements can be enhanced. In addition, the mechanical load on the WDS can be alleviated.

Other objects and features of the invention will appear in the course of the description thereof, which follows.

DESCRIPTION OF THE PREFERRED EMBODIMENTS

Embodiments of the present invention are hereinafter described with reference to the accompanying drawings.

Figure 1:
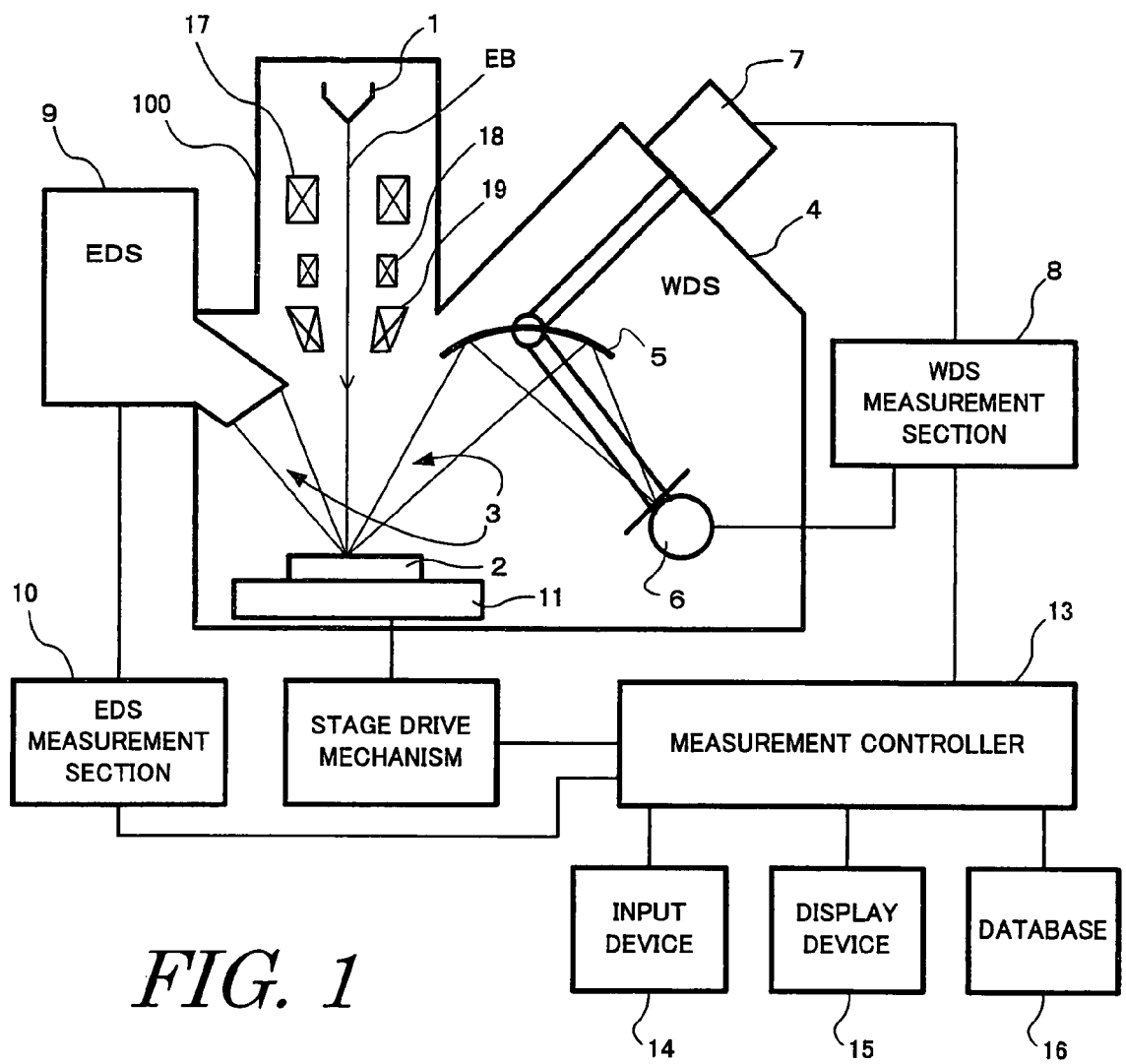
FIG. 1 is a schematic block diagram of an electron probe microanalyzer (EPMA) for embodying the present invention.

FIG. 1 schematically shows an electron probe microanalyzer (EPMA) for embodying the present invention. The microanalyzer has a microscope column 100 within which an electron gun 1 emitting an electron beam EB is disposed. The beam EB is sharply focused by condenser lenses 17 and an objective lens 19 and is directed at a sample 2. A scanning coil 18 scans the beam in two dimensions, and can vary the beam position on the sample. X-rays 3 produced from the sample 2 are spectrally analyzed and detected by a wavelength-dispersive spectrometer (WDS) 4 and an energy-dispersive spectrometer (EDS) 9. The WDS 4 includes an analyzing crystal 5, a detector 6, and a WDS drive mechanism 7. The WDS 4 is controlled via a WDS measurement section 8. Also, signals are accepted from the WDS 4 via the WDS measurement section 8. In order to mount plural wavelength-dispersive spectrometers, further wavelength-dispersive spectrometers of the same structure as the WDS 4 are necessary. Usually, only one EDS 9 is mounted.

The position of the electron beam EB on the sample 2 (i.e., analysis point) placed on a sample stage 11 can be moved in the horizontal directions (X, Y) and in the heightwise direction (Z) by a stage drive mechanism 12. The WDS measurement section 8, an EDS measurement section 10, and stage drive mechanism 12 are connected with a measurement controller 13, which provides control and accepts signals necessary for measurements. A pulse height analyzer (PHA) as described previously is mounted in the WDS measurement section 8. Input devices 14, such as a keyboard and a computer mouse, a display device 15 such as a liquid crystal monitor, and a storage device including a database 16 are connected with the measurement controller 13. The database 16 includes a compound database in which compounds are registered according to the features of their chemical compositions. Furthermore, analytical conditions (such as background measurement wavelengths interrelated with the compounds and PHA operating conditions) under which quantitative analysis is performed by the WDS are stored.

Actual instrumentation includes a vacuum pumping system for maintaining the inside of the microscope column 100 at a high degree of vacuum such as of the order of $10^{-3}$ Pa, a secondary electron detector, a backscattered electron detector, a power supply, and a DA-AD converter. Because these components are not directly associated with the understanding of the present invention, their description is omitted herein.

Figure 2:
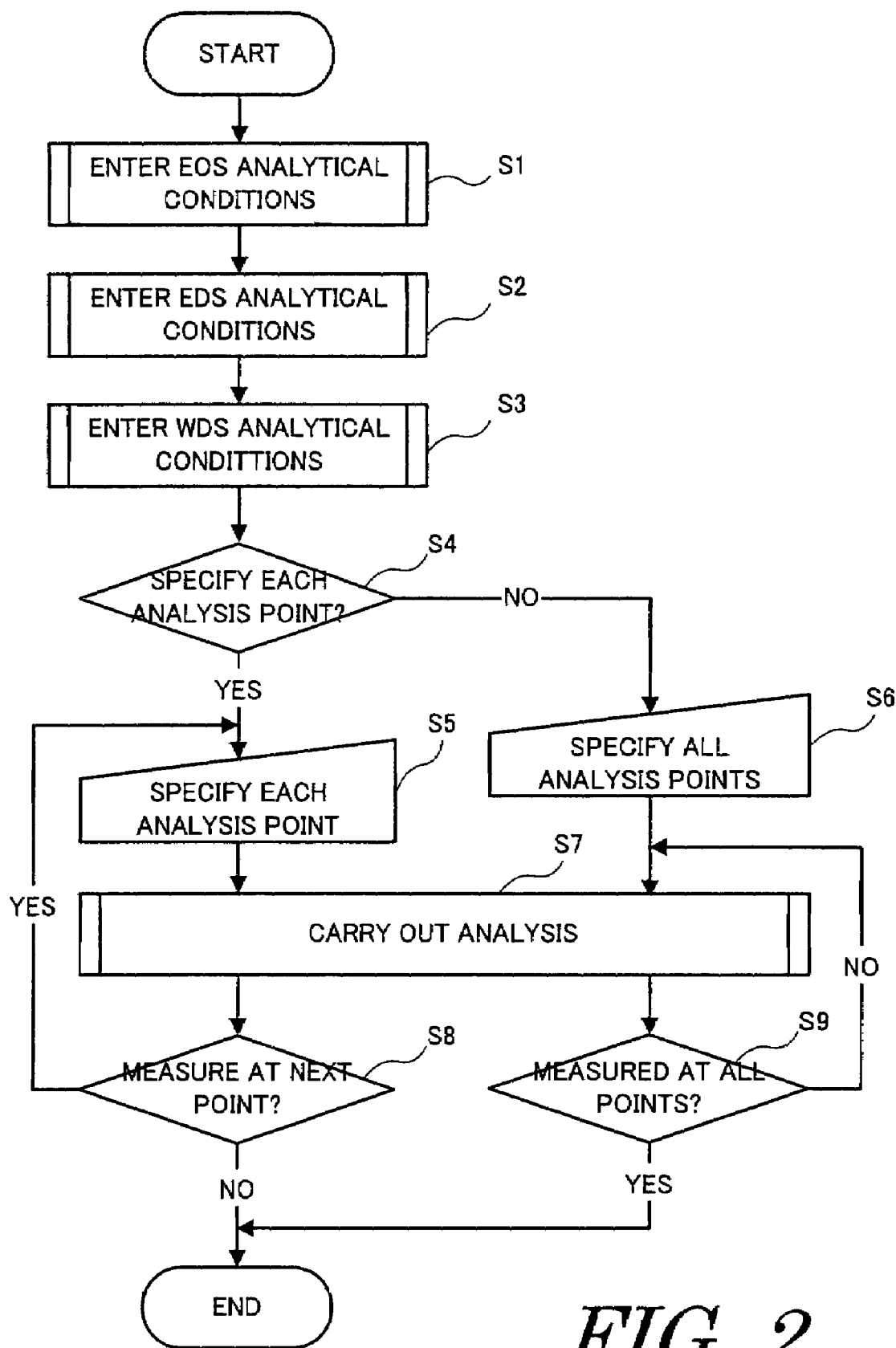
FIG. 2 is a flowchart schematically illustrating a sequence of operations performed by the EPMA shown in FIG. 1 to implement the present invention.

FIG. 2 is a flowchart schematically illustrating a sequence of operations performed to implement the present invention. The contents of the processing steps are described below.

Figure 3:
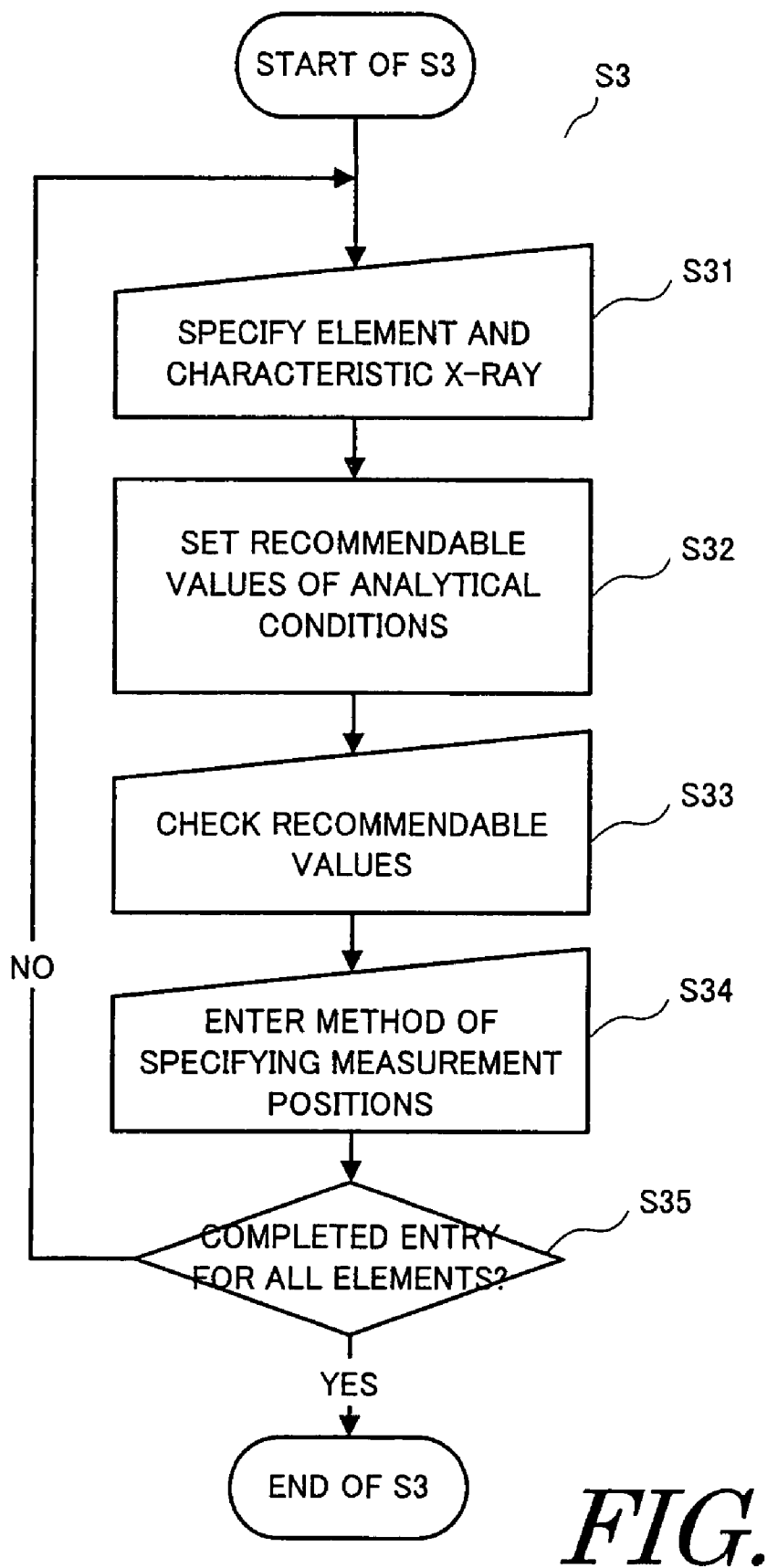
FIG. 3 is a flowchart particularly illustrating step S3 of FIG. 2 to enter analytical conditions under which a WDS performs analysis.

In step S1, a human operator enters analytical conditions for the electron optics system (EOS) such as accelerating voltage, emission current, and electron beam diameter, using the input devices 14. In step S2, the operator enters EDS analytical conditions such as measured energy range, time constant, count time, and diameter of the X-ray incident aperture, using the input devices 14. In step S3, the operator enters WDS analytical conditions, using the input devices 14. Details of step S3 are illustrated in FIG. 3.

In step S4, the measurement controller 13 makes a decision as to whether control goes to step S5 or step S6 according to a method of specifying a measurement position at an analysis point. Where a measurement position is specified at each analysis point, control goes to step S5, where the operator specifies a measurement position at each analysis point. The method of specifying a measurement position at an analysis point is well known to those skilled in the art and so its detailed description is omitted.

In step S7, the measurement controller 13 carries out analysis of the specified analysis point. Where analysis of other analysis points is performed, control goes back to step S5 from step S8. Where measurement points at all the analysis points are previously specified, control goes to step S6, where the operator specifies measurement positions at all the analysis points. In step S7, the measurement controller 13 carries out an analysis. The step S7 is repeated until analysis of all the analysis points ends. Details of step S7 are illustrated in FIG. 4.

Where the present invention is applied to particle analysis described in Japanese Patent Laid-Open No. 2001-27621, paragraph 0002, the operator does not specify measurement points at analysis points in step S5. Rather, the positions of particles on a sample surface detected by particle analysis automatically become measurement positions where analysis is performed in step S7.

Details of step S3 are next described by referring to FIG. 3. In step S31, the operator specifies an element to be analyzed and characteristic X-ray species using the input devices 14. In step S32, the measurement controller 13 sets recommended values of the analyzing crystal used for analysis, spectral wavelength position, high voltage on the detector, and counting time, and indicates whether measurement of the background intensities is made, based on the specified element and characteristic X-ray species. The specified presence or absence of the background intensity measurement is referenced in step S78 of FIG. 4 which will be described later. In step S33, the operator checks the recommended values set in step S32. If necessary, some values are reentered. In step S34, the operator enters a method of specifying measurement positions at analysis points. In step S35, the measurement controller 13 makes a decision as to whether data entry has been completed for all the elements. Control returns to step S31 unless the entry is completed. The method of specifying measurement positions at analysis points is not always required to be implemented in step S3. The method may be implemented in any stage of process performed before step S3 ends.

Figure 4:
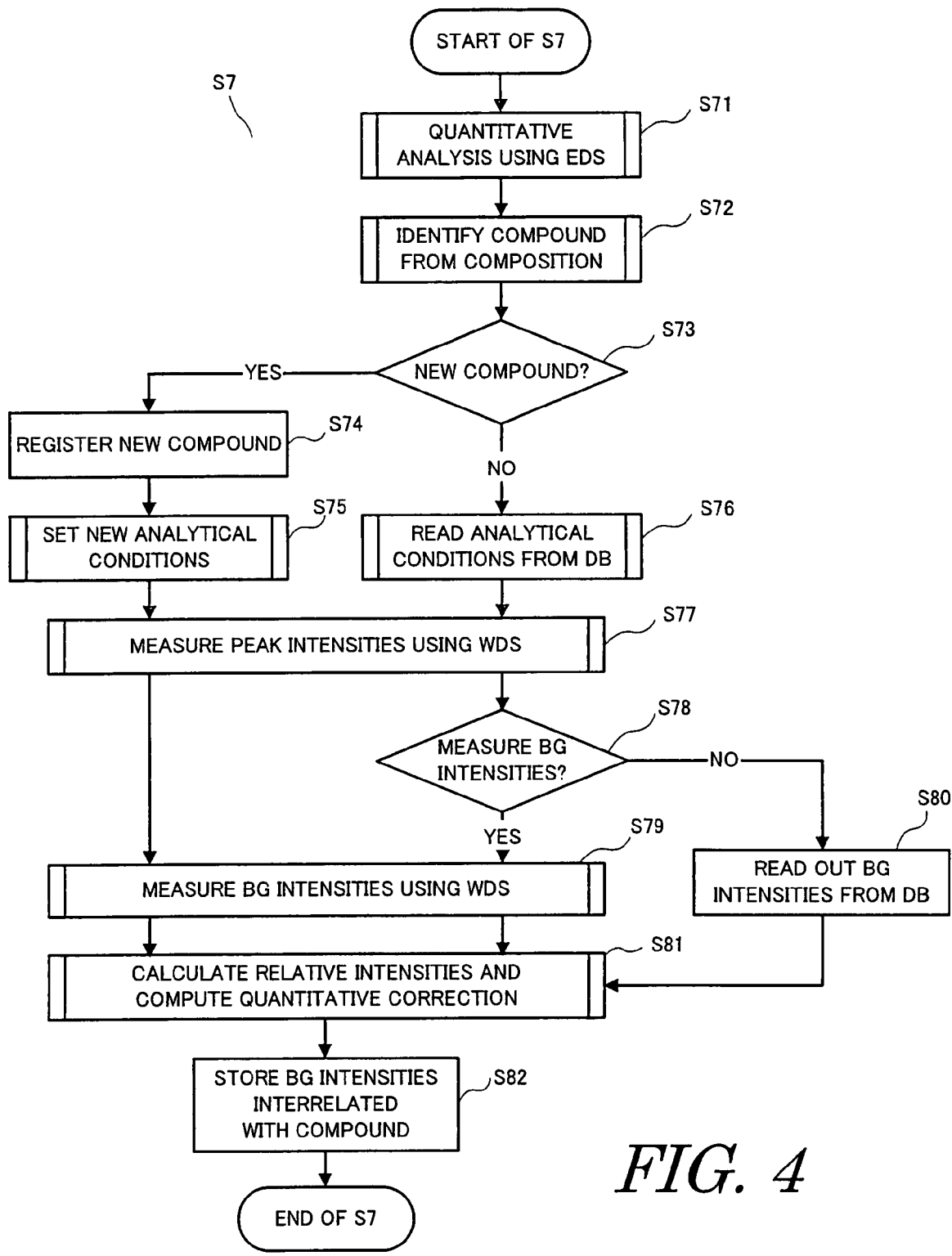
FIG. 4 is a flowchart particularly illustrating step S7 of FIG. 2 to perform analysis.

Details of step S7 are next described by referring to FIG. 4. Step S7 includes the principal routine associated with the present invention. In step S7, the operator performs no intervening manual operation. All the operations are performed under control of the measurement controller 13.

In step S71, quantitative analysis using EDS is carried out under the EDS analytical conditions entered in step S2 of FIG. 2.

Then, in step S72, the compounds at the analysis points are identified from the compositions found in step S71. For the identification, a compound database previously prepared in the database (DB) 16 (FIG. 4) and the technique disclosed in Japanese Patent Laid-Open No. 2000-266700 can be used.

In step S73, a decision is made as to whether the compounds identified in step S72 have been already registered in the database 16. If there are new compounds, control goes to step S74, where the new compounds are registered in the compound database within the database 16. Then, control proceeds to step S75, where background intensity measurement wavelengths and PHA operating conditions are determined, taking account of interfering lines. At this time, analytical conditions adapted for new compounds are set by the measurement controller 13 instead of the operator, using the techniques disclosed in Japanese Patent No. 3,547,310 and Japanese Patent Laid-Open No. H2-25787. The analytical conditions determined in step S75 are interrelated with the compounds registered in step S74 and stored in the database 16. Where the identified compounds have been already registered, control goes to step S76, where analytical conditions stored in an interrelated manner to the compounds are read from the database 16.

Then, in step S77, the peak intensities of the characteristic X-rays of the elements are measured under the analytical conditions entered in step S3. In step S79, the background intensities (FIG. 4) are measured. Where the background intensities at the analysis points have been measured and resulting data has been stored, a decision is made as to whether measurement of the background intensities is made or not, according to the instructions in step S32 in FIG. 3 as to presence or absence of background intensity measurement.

Where the measurement should be performed, control goes to step S79. Where the measurement is not performed, control proceeds to step S80. In step S80, background (BG) intensities already stored are read out. Control goes to step S81 without measuring the background intensities. Conceivable cases where the background intensities are measured at each analysis point even if there are background intensities already stored include a case where variations in background intensity are taken into consideration because the shape of sample particles or surface morphology is not good. Of course, at an analysis point judged to have a new compound, control always goes to step S79, where the background intensities are measured. In step S81, the background (BG) intensities are subtracted from the peak intensities. The relative intensity is calculated. Also, computation for quantitative correction is performed. Since the contents of the processing of step S81 are obvious to those skilled in the art, its detail description is omitted.

Then, in step S82, the analytical conditions and the measured background (BG) intensities are interrelated with the compounds and stored. The analytical conditions stored in step S82 are used in step S76. The measured background (BG) intensities in step S79 are used in step S80. The means storing the measured background intensities may be the database 16 or may utilize a storage portion normally prepared in the measurement controller 13.

While an embodiment of the present invention has been described so far, the invention is not limited thereto. In the above embodiment, the background intensity measurement wavelength and the set of PHA operating conditions are both determined within the WDS analytical conditions according to the results of the identification of compounds. Only one of the measurement wavelength and the set of PHA operating conditions may be determined.

For example, in the above description, the wavelength positions at which peak intensities (hereinafter may be abbreviated as the "peak intensity measurement wavelengths") are measured are not varied during analysis. If a new compound is identified based on the results of the identification of compounds, the peak intensity measurement wavelengths may be varied by the condition-setting means by detecting peak positions. The function of detecting peak positions is also known as "peak search" and normally equipped in a computer-controlled electron probe X-ray analyzer. The peak measurement wavelengths are varied for the following reason. Even where substances have the same elements, if the elements are chemically bonded differently for each different substance, the peak wavelength positions of the characteristic X-rays from the elements may be different for each different substance. This phenomenon is known as chemical shift.

In particular, at least one of (i) background intensity measurement wavelengths, (ii) PHA operating conditions, and (iii) peak measurement wavelengths may be determined within the WDS analytical conditions according to the results of identification of compounds. At this time, the results of measurement to be stored in the storage means need to include at least the measured background intensities.

The EDS used in the above embodiment is not limited to an X-ray spectrometer using a conventional Si(Li) semiconductor detector. For example, the EDS may also be an energy-dispersive X-ray spectrometer (such as a microcalorimeter or silicon-drifted X-ray detector) which directly extracts an electrical signal proportional to the X-ray energy from the detector without performing X-ray diffraction and performs detection using a multichannel analyzer.

As described so far, where many analysis points where plural compounds are mixed are quantitatively analyzed by WDS, the compounds are identified at each analysis point from the results of quantitative analysis using EDS permitting easy and quick analysis. Based on the results of the identification, analytical conditions adapted for the compounds are selected, and quantitative analysis using WDS is performed. Thus, the work which would have been done with heavy burden on the operator to specify background intensity measurement wavelengths and PHA operating conditions can be performed more easily than heretofore. The background intensity measurement wavelengths not affected by interfering lines can be set correctly for each compound, and quantitative analysis can be performed automatically. Furthermore, the measurement time can be shortened by omitting measurement of background intensities. This can also create the advantage that the mechanical load on the WDS can be reduced.

Having thus described my invention with the detail and particularity required by the Patent Laws, what is desired protected by Letters Patent is set forth in the following claims.

The invention claimed is:

1. An electron probe X-ray analyzer for analyzing a sample by directing a sharply focused, accelerated electron beam at the sample and detecting produced characteristic X-rays, said electron probe X-ray analyzer comprising:

WDS quantitative means for performing quantitative analysis using a wavelength-dispersive X-ray spectrometer (WDS);

EDS quantitative means for performing quantitative analysis using an energy-dispersive X-ray spectrometer (EDS);

identification means for identifying compounds at analysis points from results of quantitative analysis performed by the EDS quantitative means;

condition-setting means for setting analytical conditions to be applied to the quantitative analysis performed by the WDS quantitative means at the analysis points based on results of identification of the compounds performed by the identification means on the basis of results of the quantitative analysis performed by the EDS quantitative means; and storage means for storing (i) the compounds at the analysis points identified by the identification means, (ii) the analytical conditions set by the condition-setting means, and (iii) results of the measurement at the analysis points performed under the analytical conditions set by the condition-setting means such that these three sets of items are interrelated.

2. An electron probe X-ray analyzer as set forth in claim 1, wherein said identification means compares the results of the quantitative analysis obtained by the EDS quantitative means against a compound database to identify the compounds at the analysis points, the database containing data about compounds identified based on information about chemical compositions characterizing the compounds.

3. An electron probe X-ray analyzer as set forth in claim 1 or 2, wherein the analytical conditions set by said condition-setting means based on the results of the identification of compounds identified by the identification means and stored in the storage means are used as analytical conditions under which quantitative analysis of a next analysis point is performed by WDS quantitative means.

4. An electron probe X-ray analyzer as set forth in claim 1 or 2, wherein the analytical conditions set by said condition-setting means include at least one of (i) PHA operating conditions under which a pulse height analyzer is set to remove wavelength positions at which background intensities are measured and higher-order diffraction lines and (ii) the positions of the wavelengths at which peak intensities are measured and determined by detection of peak wavelength positions.

5. An electron probe X-ray analyzer as set forth in claim 1 or 2, wherein the results of the measurement of the analysis points measured under the analytical conditions set by said condition-setting means include at least background intensities measured at the background intensity measurement wavelength positions.

6. An electron probe X-ray analyzer as set forth in claim 1 or 2, wherein said WDS quantitative means makes a decision as to whether measurement of the background intensities is performed or not, based on information about the identification of compounds at the analysis points identified by said identification means.

7. An electron probe X-ray analyzer as set forth in claim 6, wherein when the decision is made as to whether measurement of background intensities is performed or not, the measurement of the background intensities is omitted when the compounds at the analysis points identified by said identification means have been already registered in the compound database.

* * * * *